United States Patent [19]

Geyer et al.

[11] Patent Number: 5,310,961

[45] Date of Patent: * May 10, 1994

[54] NEOMORPHIC IBUPROFEN

[75] Inventors: Robert P. Geyer, Brookline, Mass.; Vinod V. Tuliani, Media, Pa.

[73] Assignee: Affinity Biotech, Inc., Boothwyn, Pa.

[ * ] Notice: The portion of the term of this patent subsequent to May 10, 2011 has been disclaimed.

[21] Appl. No.: 87,573

[22] Filed: Jul. 2, 1993

[51] Int. Cl.⁵ .......................................... C07C 53/134
[52] U.S. Cl. .................................................. 562/496
[58] Field of Search ........................................ 562/496

[56] References Cited

U.S. PATENT DOCUMENTS

| | | |
|---|---|---|
| 3,625,711 | 12/1971 | Eisenstadt ................ 99/141 A |
| 4,049,699 | 9/1977 | Sinkula ....................... 560/105 |
| 4,049,700 | 9/1977 | Sinkula ....................... 560/105 |
| 4,361,580 | 11/1982 | Peck et al. .................... 424/287 |
| 4,609,542 | 9/1986 | Panoz et al. .................... 424/19 |
| 4,726,966 | 2/1988 | Kawashima et al. ........ 427/213.36 |
| 4,835,186 | 5/1989 | Reuter et al. ................ 514/570 |
| 4,835,188 | 5/1989 | Ho et al. ..................... 514/570 |
| 4,867,970 | 9/1989 | Newsham .................... 424/81 |
| 4,904,477 | 2/1990 | Ho et al. ..................... 424/465 |
| 4,911,921 | 3/1990 | Denton et al. ................ 424/80 |
| 4,916,161 | 4/1990 | Patell ......................... 514/570 |
| 4,954,325 | 9/1990 | Rubin et al. ................. 423/328 |
| 4,980,170 | 12/1990 | Schneider .................... 424/451 |
| 4,994,604 | 2/1991 | Tung et al. .................... 562/401 |
| 5,013,716 | 5/1991 | Cherukuri .................... 514/23 |
| 5,024,997 | 7/1991 | Motola et al. ................. 514/58 |
| 5,028,431 | 7/1991 | Franz et al. .................. 424/449 |
| 5,045,565 | 9/1991 | Gardner et al. ............... 514/487 |
| 5,059,626 | 10/1991 | Park et al. .................... 514/658 |
| 5,099,030 | 3/1992 | Gardner et al. ............... 548/478 |
| 5,191,114 | 3/1993 | Chen ......................... 562/496 |

OTHER PUBLICATIONS

Nozawa, Y et al Funtai Kogaku Kaishi 29(6) 460-4 1992.

Vinod Labhasetwart, et al., *Studies On Some Crystalline Forms Of Ibuprofen*, Drug Development and Industrial Pharmacy, 19(6), 631-641 (1993).

Primary Examiner—Paul J. Killos
Attorney, Agent, or Firm—Woodcock Washburn Kurtz Mackiewicz & Norris

[57] ABSTRACT

A novel neomorphic form of ibuprofen and processes for preparing the ibuprofen are provided. The neomorphic form is characterized by having a distinctively less bitter taste and causes less burning sensation upon swallowing. The neomorphic form of ibuprofen is an amorphous ibuprofen and is prepared by imparting kinetic energy to supercooled ibuprofen.

25 Claims, 5 Drawing Sheets

NEOMORPHIC IBUPROFEN

FIELD OF THE INVENTION

The present invention relates to a novel form of ibuprofen characterized by having a distinctively less bitter and acidic taste than is normally associated with conventional ibuprofen. More specifically, the invention relates to a novel neomorphic form of ibuprofen.

BACKGROUND OF THE INVENTION

Ibuprofen is one of the most popular non-steroidal anti-inflammatory drugs available today. Conventional ibuprofen is known to have a distinctly bitter, acidic, foul taste and to cause a burning sensation in the mouth and throat upon oral administration. Therefore, various attempts have been made to mask the taste of ibuprofen, the most common being to coat the ibuprofen in a tablet form for oral administration without chewing, usually accompanied with liquids to aid the swallowing, thus hiding the unpleasant taste of the free acid.

Unfortunately, a substantial portion of the population cannot swallow a tablet form of a drug and this is particularly true in the young and aged. These individuals commonly take such drugs in a liquid form, however the foul taste of ibuprofen in liquid form will most likely preclude compliance among these individuals.

Various attempts have been made to mask the taste of ibuprofen. The most common attempts incorporate the use of taste-masking agents with the ibuprofen, accompanied in many cases by costly production procedures. Examples of these prior efforts include admixing hydroxypropyl methylcellulose phthalate with the ibuprofen in a wet granulation process as shown in U.S. Pat. No. 4,916,161; spray drying a dispersion of ibuprofen, ethyl cellulose, and a plasticizer as shown in U.S. Pat. No. 4,835,188; dissolving ibuprofen with acrylic acid resin in an organic solvent and water to provide a granulated ibuprofen as shown in U.S. Pat. No. 4,726,966; and spray drying ibuprofen in a suspension of colloidal silica, alcohol, and cellulose acetate as shown in U.S. Pat. No. 4,835,186. Various attempts have also been made to alter the chemical structure of ibuprofen to a form that has a less objectionable taste as shown in U.S. Pat. Nos. 4,049,699 and 4,361,580, however the utility of these forms remains to be determined.

There still exists a need in the art to develop a taste-masked form of ibuprofen which can be prepared easily and does not require the additional blending of specific amounts of certain taste-masking agents.

SUMMARY OF THE INVENTION

The present invention provides an improved tasting neomorphic form of ibuprofen and methods for its preparation. This new form of ibuprofen is characterized by having an amorphous structure. By "amorphous" is meant that the neomorphic form of ibuprofen has no defined crystalline structure characteristic of conventional ibuprofen. This characteristic is easily determined by visual inspection using microscopic means and by birefringence testing, by which the neomorphic form exhibits substantially no birefringence while the conventional crystalline form exhibits marked birefringence.

The neomorphic form generally has a roughly irregular particle shape; the particles are substantially equiaxial and the number average ratio of the longer axis to the shorter axis of the particles is less than about 3:1, preferably less than about 3:2. The neomorphic ibuprofen particles, on a number average basis, preferably have an averaged particle size of greater than about 100 microns and generally less than about 500 microns. By "averaged particle size" is meant the average of the diameter of the particles along their longest axis and shortest axis. The ibuprofen particles are thus distinct morphologically from conventional ibuprofen which is characterized by having a rod-like crystalline structure, being usually about 100 microns in length and up to about 20 microns in width, and thus have an averaged particle size of less than about 100 microns, although this can vary depending upon the particular manufacturer.

The neomorphic ibuprofen can be prepared by various methods. Common to the methods is the alteration of the normal resolidification of the ibuprofen from an ibuprofen melt, which resolidification ordinarily yields crystalline ibuprofen. The methods are performed by first providing ibuprofen in a supercooled state. Typically, the ibuprofen is heated past its melting point resulting in a molten ibuprofen. This molten ibuprofen is then cooled below its melting point while maintaining the molten condition, thus achieving a supercooled ibuprofen state.

The method for the resolidification of the supercooled ibuprofen into the improved tasting ibuprofen requires some form of energy, in the form of kinetic energy, to be imparted into the supercooled ibuprofen. The amorphous ibuprofen is then recovered. It is preferred to continue the application of the kinetic energy until a majority of the ibuprofen is converted to the amorphous form. This method can be conducted at various temperatures below the melting point of the ibuprofen.

A further method for the preparation of the neomorphic ibuprofen is to provide the molten, supercooled ibuprofen in a fluid that disperses the supercooled ibuprofen as a discrete molten phase, preferably an internal dispersed phase. Kinetic energy is imparted into the mixture containing the dispersed ibuprofen to convert the supercooled ibuprofen into solid amorphous ibuprofen which is then recovered. The process can be operated in a batch-wise or continuous fashion with the recycling of the dispersant fluid.

DETAILED DESCRIPTION OF THE INVENTION

Figure 1:
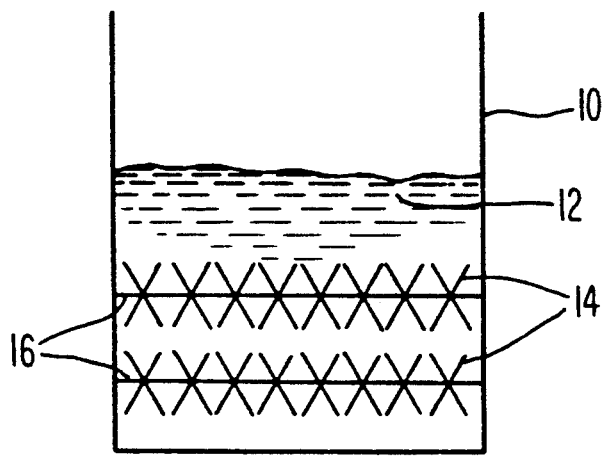
FIG. 1 is a cut-away view of a reaction vessel for performing the methods of the present invention.

The present invention relates to a neomorphic form of the non-steroidal anti-inflammatory drug (NSAID) ibuprofen and preparatory methods for making the same. Conventional ibuprofen is characterized by its bitter taste upon mastication and burning sensation upon swallowing. The neomorphic form of ibuprofen of the present invention is characterized by having a bland or neutral taste and also a greatly reduced burning sensation felt at the back of the throat upon swallowing of the drug. Thus the neomorphic form is ideally suited for administration of ibuprofen in any format, especially in a format other than in a taste-coated tablet that is to be swallowed without contact of the drug with the mouth or throat. Such administration forms include powders or tablets that can be chewed, liquid suspensions for drinking, or in some form that allows for the contacting of the ibuprofen with the mouth or throat.

Conventional ibuprofen, as used herein, refers to the chemical compound that has been chemically named $\pm$2-(p-isobutylphenyl)propionic acid, 2-(4-isobutylphenyl)propionic acid, p-(iso-butyl)hydrotropic acid, and $\alpha$-methyl-$\alpha$-(p-isobutylphenyl)acetic acid, either as a racemic mixture or as either of its + or − isomers.

The present neomorphic form of ibuprofen is chemically similar to the conventional form of ibuprofen, but is different with respect to its physical characteristics and taste characteristics.

The neomorphic ibuprofen of the present invention can be produced in a wide variety of ways employing common physical and chemical characteristics of ibuprofen. The production process takes advantage of the supercooled state of ibuprofen and the ability of ibuprofen to resolidify into the amorphous form under conditions that inhibit recrystallization.

In one method of production the resolidification requires the application of energy to the molten, supercooled ibuprofen. In broad terms, the process encompasses providing ibuprofen in a supercooled state, imparting energy, preferably kinetic energy, into the molten ibuprofen for a time and intensity sufficient to convert the molten ibuprofen into the solid neomorphic ibuprofen, and recovering the resultant product.

In this method the ibuprofen is heated above its melting point of about 74°–77° C., so the heating is preferably above about 75° C., more preferably from about 75°–80° C., resulting in a molten ibuprofen. This molten ibuprofen is then cooled to below its melting point to a process temperature of below about 65° C. to take advantage of the lower viscosity at elevated temperatures, and preferably the temperature is maintained below about 60° C., more preferably below about 55° C., due to the release of heat upon resolidification and thus the possibility of the ibuprofen again passing into the molten state as kinetic energy is supplied. The resolidification can, of course, be conducted at various lower temperatures, however preferably above about −40° C., more preferably above about −30° C. In general practice, the process temperature is from about −20° C. to about 65° C., preferably from about 0° C. to about 45° C., more preferably from 0° C. to 35° C., and most preferably from 0° C. to 25° C. Preferably, agitation is minimized during the cooling of the molten ibuprofen to the supercooled state and to the process temperature to minimize any premature resolidification into the crystalline state.

A low temperature process for preparing amorphous ibuprofen is disclosed in a co-pending application entitled "Low Temperature Process for Preparing Neomorphic Ibuprofen" in the name of the inventors of this application, application Ser. No. 08/086922, filed Jul. 2, 1993. That application is incorporated herein in its entirety by reference.

The type of kinetic energy imparted into the supercooled ibuprofen will be dependent upon the type of processing system used to handle the manufacture. The kinetic energy is applied to the supercooled ibuprofen for a time and intensity sufficient to cause resolidification into the neomorphic form. It is preferred that the kinetic energy be applied for a time and intensity sufficient for at least about 50 weight percent, preferably 70 weight percent, more preferably at least 90 weight percent, and most preferably at least 95 weight percent, of the supercooled ibuprofen to be solidified into the neomorphic state. It is noted that if the kinetic energy is discontinued during the resolidification process, or if the energy is not sufficiently intense, then the supercooled ibuprofen can recrystallize on its own into the conventional form of ibuprofen having unpleasant taste characteristics.

Manufacture of the neomorphic ibuprofen in a batchwise manner can be accomplished by containing the supercooled ibuprofen in an appropriate vessel. Preferred vessels include plastic vessels capable of transmitting the kinetic energy effectively to the supercooled ibuprofen and having a surface which favors the production of the neomorphic ibuprofen. The kinetic energy can then take the form of, for example, physically striking the vessel walls or vigorously stirring or striking the supercooled ibuprofen for a time and intensity sufficient to form the neomorphic ibuprofen. The vessel can be equipped with "seeding surfaces" made of appropriate materials which can take the form of any type of exposed surface inside the vessel upon which the supercooled ibuprofen can resolidify. As shown in FIG. 1, the vessel 10 containing the supercooled ibuprofen 12 can contain seeding surfaces 14, shown here as rod-like protrusions supported by bars 16.

A further process for the production of neomorphic ibuprofen is to disperse ibuprofen, either before or after attaining the supercooled state, in a dispersing fluid. Particulate ibuprofen can be added to the dispersing fluid and this dispersion can be brought to a temperature to melt the ibuprofen, or the dispersing fluid can be admixed to the molten or supercooled ibuprofen. The dispersing fluid can be broadly defined as any fluid in which the molten ibuprofen can be dispersed without materially altering the chemical nature of the ibuprofen and in which the ibuprofen has a relatively low solubility. Kinetic energy is then imparted into this supercooled ibuprofen dispersion for a time and intensity sufficient to convert the ibuprofen into its neomorphic form. The neomorphic ibuprofen is then recovered by, for example, filtering or evaporating the dispersing fluid. The process can proceed in batch-wise or continuous fashion. It is preferred that the kinetic energy supplied be in the form of physically shaking a vessel containing the dispersion mixture, or by stirring the dispersion, or by pumping the mixture into a barrier. Suitable dispersing fluids include glycerol and water, among others. The dispersing fluid can be recycled back into the production process after it is separated from the neomorphic ibuprofen. The yields of neomorphic ibuprofen are similar to the yields for the kinetic energy process without the dispersing fluid.

Figure 2:
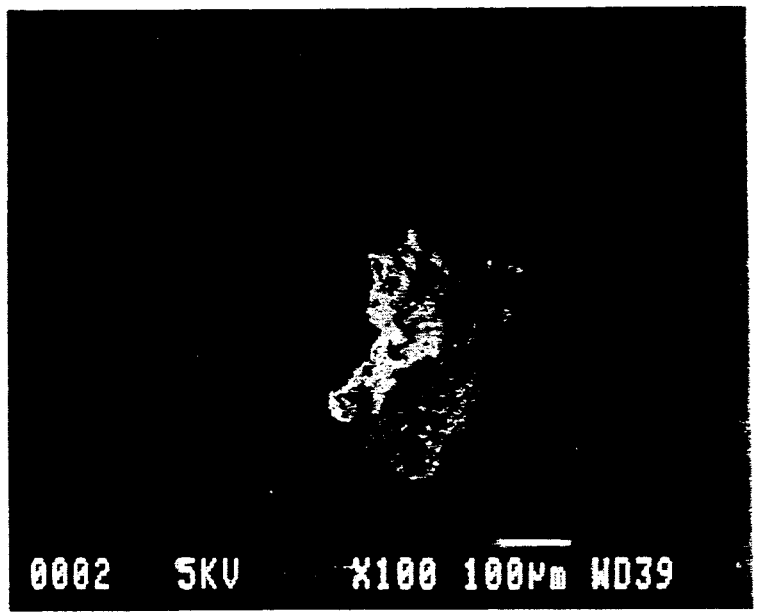
FIG. 2 is a photomicrograph of the neomorphic ibuprofen of the present invention taken at 100× magnification using a scanning electron microscope with a line legend of 100 microns.
Figure 3:
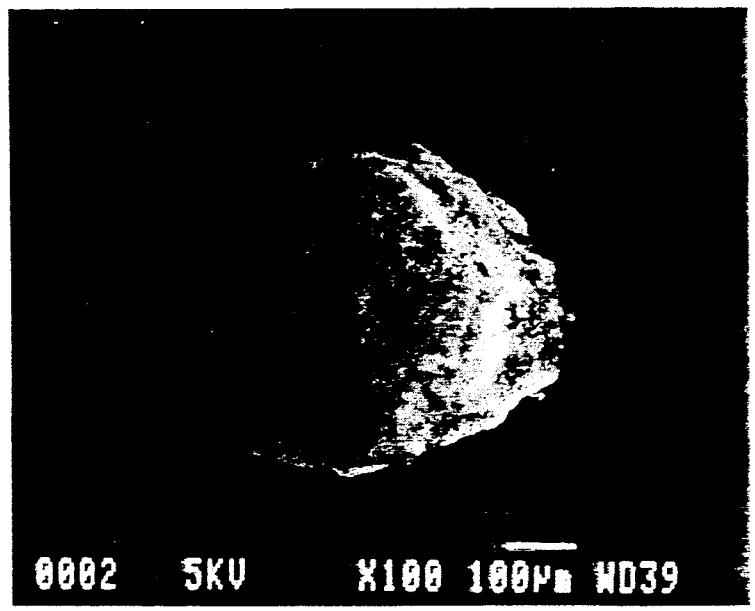
FIG. 3 is a second photomicrograph of the neomorphic ibuprofen of the present invention taken at 100× magnification using a scanning electron microscope with a line legend of 100 microns.
Figure 4:
FIG. 4 is a photomicrograph of conventional ibuprofen taken at 100× magnification using a scanning electron microscope with a line legend of 100 microns.

Neomorphic ibuprofen can be described by its distinguishing physical features in relation to conventional ibuprofen. Conventional ibuprofen is characterized by its crystalline structure, while neomorphic ibuprofen has an amorphous structure. Amorphous ibuprofen prepared by the methods of the present invention is generally characterized by having a roughly irregular shape as shown in FIGS. 2-3. Generally, the ratio of the length of the longest axis to the shortest axis of the amorphous ibuprofen particles is less than about 3:1, preferably less than about 2:1, more preferably less than about 1.5:1, on a number average basis. The amorphous form of ibuprofen is distinct from the conventional form of ibuprofen, FIG. 4, which has a rod-like crystalline structure with a length of about 100 microns and a width of about 20 microns, and thus has an averaged particle size of about 60 microns on a number average basis and a longest:shortest axis ratio of about 5:1. The amorphous neomorphic ibuprofen particles preferably have an averaged particle size of greater than about 100 microns, preferably greater than about 200 microns, more preferably greater than about 300 microns, and generally in the range of from about 100 to about 600 microns, preferably from about 200 to about 600 microns, on a number average basis.

The "averaged particle size" is determined by taking the average of the measurements of the length of the longest axis and the shortest axis of the particle. It is noted that those skilled in the art are able to determine average particle sizes and number average ratios by conventional methods such as microscopic analysis.

Figure 5:
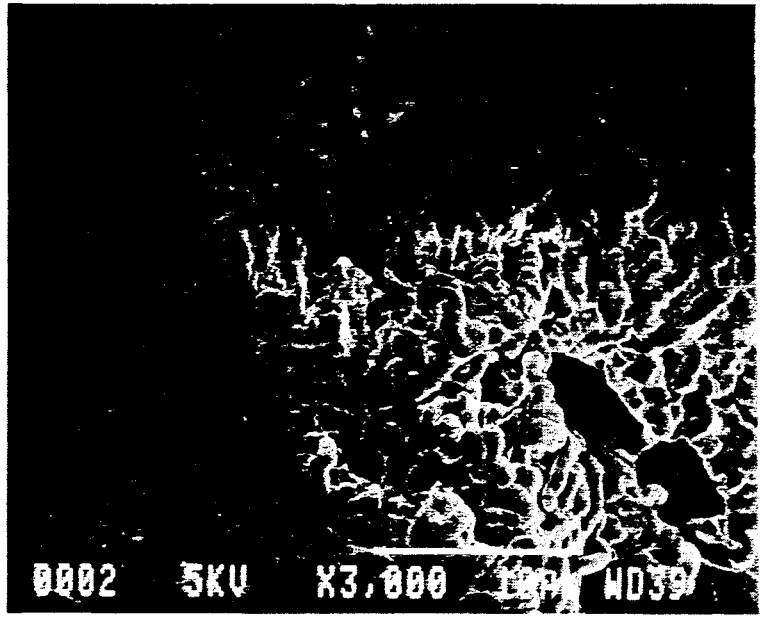
FIG. 5 is a photomicrograph of the neomorphic ibuprofen of the present invention taken at 3,000× magnification using a scanning electron microscope with a line legend of 10 microns.
Figure 6:
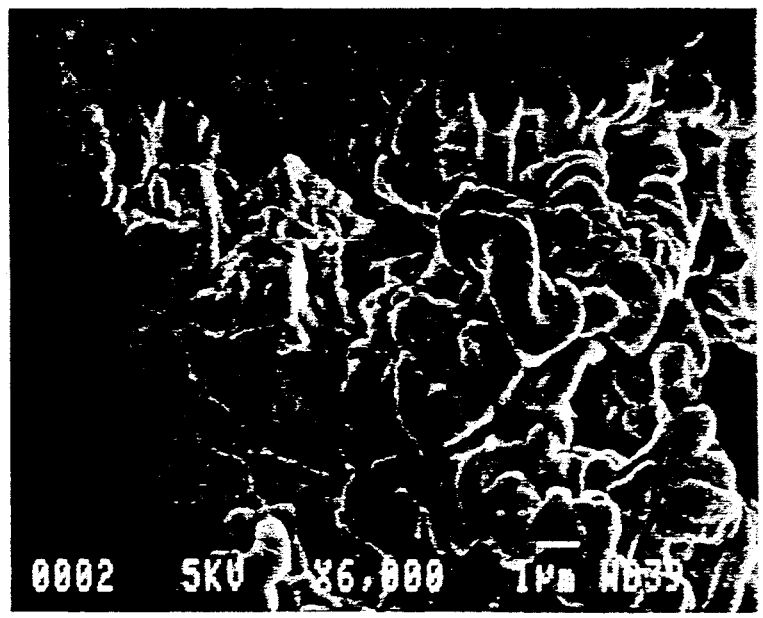
FIG. 6 is a photomicrograph of the neomorphic ibuprofen of the present invention taken at 6,000× magnification using a scanning electron microscope with a line legend of 1 micron.
Figure 7:
FIG. 7 is a photomicrograph of conventional ibuprofen taken at 3,000× magnification using a scanning electron microscope with a line legend of 10 microns.
Figure 8:
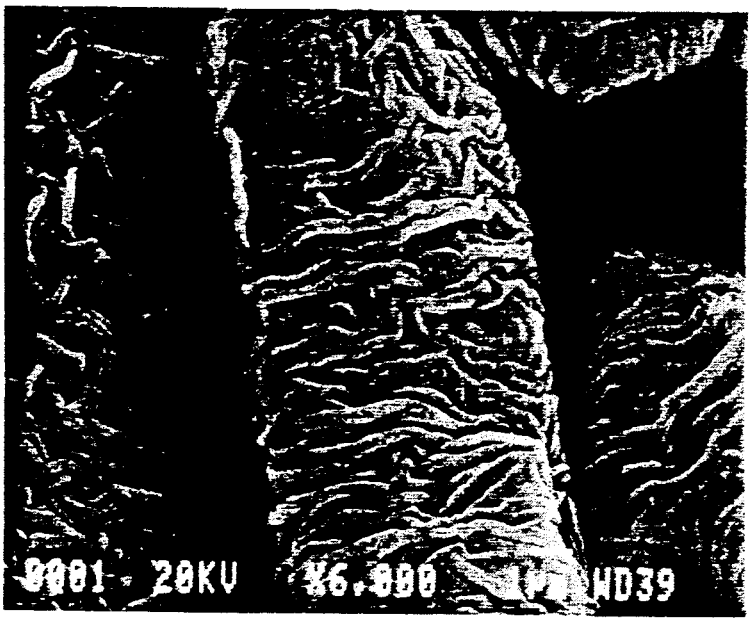
FIG. 8 is a photomicrograph of conventional ibuprofen taken at 6,000× magnification using a scanning electron microscope with a line legend of 1 micron.

The surface of a neomorphic ibuprofen particle under the scanning electron microscope at a magnification of 3000× and 6000×, FIGS. 5 and 6, respectively, is fused and irregular. The surface is characterized by a multitude of grooves. The grooves on the surface of the neomorphic ibuprofen particles produced in accordance with the methods set forth herein are approximately 1-3 microns in width and approximately 5-15 microns in length and are in a contorted, twisted, nonorderly pattern. The neomorphic ibuprofen particles also frequently contain "pores" on the surface. The surface of conventional ibuprofen under the same magnification, FIGS. 7 and 8, respectively, is ordered and regular. The grooves on the surface of conventional ibuprofen crystals are approximately 0.2-0.6 microns in width and appear to generally extend around the circumference of the particle in an orderly fashion perpendicular to the long axis.

Birefringence is a characteristic common to crystalline materials. Birefringence is easily determined by viewing the material through partially or completely crossed polarized filters. Amorphous ibuprofen exhibits no birefringence and is substantially colorless when viewed through partially or completely crossed polarized lenses. Conventional ibuprofen exhibits birefringence and displays various colors when viewed through crossed polarizers.

The x-ray diffraction patterns for neomorphic and conventional ibuprofen display peaks for the two types of ibuprofen at substantially similar positions, however, the intensities of these peaks are different. It is believed that the differences in the intensities is due to the distinct orientation and morphology of the surface of two polymorphs of ibuprofen.

Generally, neomorphic ibuprofen is chemically similar to conventional ibuprofen. The infrared spectra for the neomorphic and conventional forms of ibuprofen in a potassium bromide dispersion have substantially similar peak patterns.

The neomorphic form of ibuprofen of the present invention can be masticated and swallowed in its unaltered form without the bitter taste and burning sensation caused by conventional ibuprofen. The neomorphic form can therefore be administered without the need for taste-masking or flavor enhancing additives or agents, if desired, however such components can be admixed with the neomorphic ibuprofen.

The neomorphic ibuprofen can be presented for administration with or without the above mentioned additives. Lubricants such as magnesium stearate, talc, calcium stearate, stearic acid, and hydrogenated vegetable oils, and flow control agents such as microcrystalline cellulose, microcrystalline dextrose, amylose, and polyvinylpyrrolidone can be used. The neomorphic ibuprofen can also be prepared as a liquid suspension or dispersion.

The dosage to effect the desired therapeutic result, "therapeutically effective amount", for this form of ibuprofen can be readily determined of those skilled in the art. Generally, ranges from about 100 mg to about 800 mg per dosage, which can be repeated about every 4 to 6 hours should provide acceptable responses. The various embodiments of the present invention are further described by the following nonlimiting examples.

EXAMPLE 1

Conventional ibuprofen, about 2 g, manufactured by Ethyl Corporation, was heated to molten state at a temperature of about 77° C. to 80° C. and transferred into a pliable plastic container (2 ml). The container was then placed in an ice bath for about 10 minutes until the temperature of the now supercooled ibuprofen was about 0° C. The vessel was struck repeatedly by a hammer weighing about 0.5 kg to induce the supercooled ibuprofen to resolidify. The solidification proceeded and the hammering was continued for about 5 minutes until substantially all of the ibuprofen was resolidified. The resolidified amorphous ibuprofen was found to have a noticeably less bitter taste and produced relatively little burning sensation in the mouth and throat in comparison to conventional ibuprofen.

The x-ray diffraction pattern for the amorphous ibuprofen displayed minor peaks at about 2.64, 2.80, 2.89, 3.47, 3.70, 6.06, 6.36 and major peaks at about 4.02, 4.43, 4.53, 4.67, 5.03, 5.37, and 14.5. The x-ray diffraction pattern for a sample of crystalline ibuprofen displayed minor peaks at about 2.63, 2.80, 2.89, 7.25 and major peaks at about 3.96, 4.40, 4.67, 4.72, 5.33 and 14.5.

The infrared spectra, using a potassium bromide dispersion of the samples, for the amorphous and crystalline ibuprofen were also very similar. The amorphous ibuprofen displayed peaks as indicated in Table 1.1. The crystalline ibuprofen displayed peaks as indicated in Table 1.2.

TABLE 1.1

| CM$^{-1}$ | % |
| --- | --- |
| 3822.3 | 33.11 |
| 3448.2 | 25.87 |
| 2955.9 | 14.12 |
| 2868.2 | 16.98 |
| 2728.2 | 27.45 |
| 2631.9 | 28.45 |
| 2363.7 | 43.49 |
| 1720.5 | 14.12 |
| 1560.2 | 53.61 |
| 1507.9 | 30.12 |
| 1461.9 | 30.51 |
| 1450.8 | 38.17 |
| 1419.8 | 23.46 |
| 1379.6 | 34.27 |
| 1364.4 | 43.83 |
| 1320.9 | 28.96 |
| 1268.3 | 29.70 |
| 1231.0 | 20.45 |
| 1183.4 | 26.21 |
| 1167.8 | 40.07 |
| 1122.9 | 45.86 |
| 1091.8 | 48.00 |
| 1066.8 | 38.73 |
| 1008.0 | 40.17 |
| 969.9 | 44.84 |
| 935.8 | 31.00 |
| 880.1 | 50.39 |
| 865.9 | 34.53 |
| 849.1 | 46.93 |
| 819.9 | 57.18 |
| 779.6 | 24.06 |
| 746.3 | 52.02 |
| 690.9 | 51.98 |
| 668.0 | 32.23 |
| 636.2 | 46.88 |
| 588.3 | 42.16 |
| 521.8 | 40.89 |
| 478.7 | 58.20 |

TABLE 1.2

| CM$^{-1}$ | % |
| --- | --- |
| 2955.6 | 10.89 |
| 2868.5 | 14.81 |
| 2728.7 | 25.28 |
| 2631.9 | 26.42 |
| 2360.8 | 30.74 |
| 2341.8 | 33.97 |
| 1720.6 | 7.06 |
| 1560.2 | 52.15 |
| 1507.9 | 29.57 |
| 1462.0 | 30.40 |
| 1420.1 | 21.71 |
| 1379.8 | 33.68 |
| 1364.8 | 42.88 |
| 1321.1 | 27.24 |
| 1268.2 | 28.45 |
| 1231.0 | 16.69 |
| 1183.7 | 25.28 |
| 1123.1 | 44.78 |
| 1091.9 | 46.80 |
| 1067.3 | 39.29 |
| 1007.9 | 40.25 |
| 969.8 | 43.52 |
| 935.6 | 30.38 |
| 880.1 | 48.55 |
| 865.9 | 35.03 |
| 849.0 | 45.68 |
| 819.8 | 54.33 |
| 779.7 | 25.29 |
| 746.2 | 49.62 |
| 690.5 | 49.07 |
| 668.1 | 29.70 |
| 636.1 | 44.77 |
| 588.3 | 41.35 |
| 521.5 | 39.66 |
| 478.5 | 52.85 |

EXAMPLE 2

Example 1 was repeated using the same container having about 3 stainless steel (316) wire pieces (1 cm long, 0.1 cm diameter) placed into the container. Again the amorphous ibuprofen particles recovered after the hammering had an improved taste and a decreased burning sensation in comparison to the conventional ibuprofen.

EXAMPLE 3

Conventional ibuprofen (5 g) manufactured by Ethyl Corp., was heated to a temperature of about 77° C. to 80° C. in a plastic vessel to form molten ibuprofen. A lid was securely positioned onto the vessel. The vessel was then placed in an ice bath to cool the molten ibuprofen to the supercooled state at a temperature of about 0° C. The lid was removed and about 15 ml of glycerol was added to the vessel and the lid was resecured. The vessel was shaken vigorously by hand for about 10 minutes. The slurry was poured onto a vacuum filter (Durx 770, Berkshire Corp.) without disturbing the drug that adhered to the vessel walls. The amorphous ibuprofen filtered material was washed thoroughly with water to remove the glycerol. The final product was dried at 45° C.

The neomorphic ibuprofen was then sieved through a set of sieves to yield particles of about 500 microns and smaller. These neomorphic ibuprofen particles were found to have almost no burning sensation when tasted upon mastication and swallowing during oral administration.

EXAMPLE 4

Conventional ibuprofen (5 g) manufactured by Ethyl Corp., and 15 ml glycerol were heated in a water bath for about 15 minutes at a temperature of about 77° C. to 80° C. in a plastic vessel to form molten ibuprofen. A lid was securely positioned onto the vessel. The vessel was then placed in an ice bath to cool the molten ibuprofen to the supercooled state at a temperature of about 8° C. The vessel was shaken vigorously by hand for about 10 minutes. The slurry was poured onto a vacuum filter (Durx 770, Berkshire Corp.) without disturbing the drug that adhered to the vessel walls. The amorphous ibuprofen filtered material was washed thoroughly with water to remove the glycerol. The final product was dried at 45° C.

The neomorphic ibuprofen particles were found to have almost no burning sensation when tasted upon mastication and swallowing during oral administration.

What is claimed is:

1. A bland tasting neomorphic form of ibuprofen comprising amorphous ibuprofen.

2. The neomorphic form of ibuprofen of claim 1 wherein the ibuprofen exhibits no birefringence.

3. The neomorphic form of ibuprofen of claim 2 wherein the amorphous ibuprofen comprises particles having an averaged particle size of greater than about 100 microns on a number average basis.

4. The neomorphic form of ibuprofen of claim 2 wherein the surface of the amorphous ibuprofen is a fused, irregular surface.

5. The neomorphic form of ibuprofen of claim 3 wherein the number average ratio of the longer axis to the shorter axis of the ibuprofen particles is less than about 6. The neomorphic form of ibuprofen of claim 5 wherein the amorphous ibuprofen has an averaged particle size between 100–600 microns on a number average basis.

7. The neomorphic form of ibuprofen of claim 6 wherein the surface of the amorphous ibuprofen particles is a fused, irregular surface.

8. An ibuprofen composition comprising at least, about 50 percent by weight amorphous ibuprofen of claim 1.

9. An ibuprofen composition comprising at least 70 percent by weight amorphous ibuprofen of claim 1.

10. A process for preparing neomorphic ibuprofen having a bland taste and an amorphous structure, comprising:
    (a) providing molten ibuprofen in a supercooled state;
    (b) imparting kinetic energy into the supercooled ibuprofen for a time and intensity sufficient to convert a portion of the supercooled ibuprofen into solid amorphous ibuprofen; and
    (c) recovering the solid amorphous ibuprofen.

11. The process of claim 10 wherein the amorphous ibuprofen exhibits no birefringence.

12. The process of claim 10 wherein the kinetic energy is imparted for a period of time to convert at least about 50 percent by weight of the molten ibuprofen into solid amorphous ibuprofen.

13. The process of claim 10 wherein the kinetic energy is imparted for a period of time to convert at least about 70 percent by weight of the molten ibuprofen into solid amorphous ibuprofen.

14. The process of claim 10 wherein the molten ibuprofen in the supercooled state is at a temperature below about 65° C.

15. The process of claim 14 further comprising providing the molten ibuprofen in a vessel, and wherein the imparting of kinetic energy comprises directing a mechanical force at the vessel.

16. The process of claim 15 wherein the vessel comprises seeding surfaces, and the method further comprises resolidifying the ibuprofen on said surfaces.

17. A process for preparing neomorphic ibuprofen having a bland taste and an amorphous structure, comprising:
    (a) providing a dispersion of molten ibuprofen in a supercooled state in a dispersing fluid;
    (b) imparting kinetic energy into the dispersion for a time and intensity sufficient to convert a portion of the supercooled ibuprofen into solid amorphous ibuprofen; and
    (c) recovering the solid amorphous ibuprofen.

18. The process of claim 17 wherein the amorphous ibuprofen exhibits no birefringence.

19. The process of claim 17 wherein the dispersion fluid comprises glycerol, water, or mixtures thereof.

20. The process of claim 19 further comprising separating the dispersing fluid from the solid amorphous ibuprofen.

21. The process of claim 20 further comprising recycling the separated dispersing fluid and adding the recycled fluid to the mixture of step (a).

22. The process of claim 17 wherein the imparting of kinetic energy comprises shaking the mixture.

23. A composition suitable for oral administration comprising a therapeutically effective quantity of the amorphous ibuprofen of claim 1.

24. The product of the process of claim 10.

25. The product of the process of claim 17.

* * * * *

UNITED STATES PATENT AND TRADEMARK OFFICE
CERTIFICATE OF CORRECTION

PATENT NO. : 5,310,961
DATED : 5/10/94
INVENTOR(S) : Geyer et al.

It is certified that error appears in the above-identified patent and that said Letters Patent is hereby corrected as shown below:

Column 8, line 68, after "about" insert --3:1.--

Signed and Sealed this

Eighteenth Day of April, 1995

Attest:

BRUCE LEHMAN

Attesting Officer

Commissioner of Patents and Trademarks